United States Patent
Paul

(10) Patent No.: US 8,236,033 B2
(45) Date of Patent: *Aug. 7, 2012

(54) SPINAL PLATE ASSEMBLY

(76) Inventor: Kamaljit S. Paul, Oshkosh, WI (US)

( * ) Notice: Subject to any disclaimer, the term of this patent is extended or adjusted under 35 U.S.C. 154(b) by 1355 days.

This patent is subject to a terminal disclaimer.

(21) Appl. No.: 11/893,014

(22) Filed: Aug. 13, 2007

(65) Prior Publication Data

US 2008/0033439 A1 Feb. 7, 2008

Related U.S. Application Data

(63) Continuation of application No. 10/627,137, filed on Jul. 24, 2003, now Pat. No. 7,255,699, which is a continuation-in-part of application No. 10/202,705, filed on Jul. 24, 2002, now Pat. No. 7,070,599, which is a continuation-in-part of application No. 10/014,409, filed on Dec. 14, 2001, now Pat. No. 6,755,833.

(51) Int. Cl.
*A61B 17/80* (2006.01)

(52) U.S. Cl. .......................... 606/280; 606/289

(58) Field of Classification Search .................... 606/71, 606/281–296
See application file for complete search history.

(56) References Cited

U.S. PATENT DOCUMENTS

| | | |
|---|---|---|
| 2,406,832 A | 9/1946 | Hardinge |
| 2,486,303 A | 10/1949 | Longfellow |
| 2,580,821 A | 1/1952 | Nicola |
| 2,780,223 A | 2/1957 | Haggland |
| 3,244,170 A | 4/1966 | McElvenny |
| 3,534,731 A | 10/1970 | Muller |
| 3,596,656 A | 8/1971 | Kaute |
| 3,659,595 A | 5/1972 | Haboush |
| 3,695,259 A | 10/1972 | Yost |
| 3,741,205 A | 6/1973 | Markolf et al. |
| RE28,841 E | 6/1976 | Allgower et al. |
| 4,246,660 A | 1/1981 | Wevers |
| 4,388,921 A | 6/1983 | Sutter et al. |
| RE31,628 E | 7/1984 | Allgower et al. |
| 4,484,570 A | 11/1984 | Sutter et al. |
| 4,488,543 A | 12/1984 | Tornier |
| 4,503,848 A | 3/1985 | Caspar et al. |

(Continued)

FOREIGN PATENT DOCUMENTS

DE 251246 9/1912

(Continued)

OTHER PUBLICATIONS

Blackstone Medical, Inc., Blackstone Anterior Cervical Plate, product literature, 4 pages.

(Continued)

*Primary Examiner* — Thomas C. Barrett
*Assistant Examiner* — Michael Araj
(74) *Attorney, Agent, or Firm* — Thomas D. Wilhelm; Wilhelm Law, S.C.

(57) ABSTRACT

Spinal plate assembly, and methods of use, wherein a retaining element such as a retaining band, optionally a resiliently flexible band, mounted to a spinal plate, activates a blocking feature of the spinal plate assembly to thereby prevent the bone fastener from withdrawing out of the spinal plate assembly and past the blocking member. The apertures are typically, but not necessarily, elongate slots, elongate axes of all such slots being commonly oriented. The band can be fabricated from a variety of bio-stable, bio-compatible medical grade materials, including metals or implantable plastics. The retaining element or elements can be disposed in intermittently-located channel elements in the plate.

17 Claims, 8 Drawing Sheets

U.S. PATENT DOCUMENTS

| | | | |
|---|---|---|---|
| 4,513,744 A | 4/1985 | Klaue |
| 4,794,918 A | 1/1989 | Wolter |
| 4,943,292 A | 7/1990 | Foux |
| 4,955,908 A | 9/1990 | Frey et al. |
| 4,957,497 A | 9/1990 | Hoogland et al. |
| 5,041,113 A | 8/1991 | Biedermann et al. |
| 5,085,660 A | 2/1992 | Lin |
| 5,108,395 A | 4/1992 | Laurain |
| 5,113,685 A | 5/1992 | Asher et al. |
| 5,129,903 A | 7/1992 | Luhr et al. |
| 5,147,360 A | 9/1992 | Dubousset |
| 5,147,361 A | 9/1992 | Ojima et al. |
| 5,180,381 A | 1/1993 | Aust et al. |
| 5,234,431 A | 8/1993 | Keller |
| 5,261,910 A | 11/1993 | Warden et al. |
| 5,324,290 A | 6/1994 | Zdeblick et al. |
| 5,344,421 A | 9/1994 | Crook |
| 5,364,399 A | 11/1994 | Lowery et al. |
| 5,423,826 A | 6/1995 | Coates et al. |
| 5,478,342 A | 12/1995 | Kohrs |
| 5,486,176 A | 1/1996 | Hildebrand et al. |
| 5,520,690 A | 5/1996 | Errico et al. |
| 5,520,696 A | 5/1996 | Wenstrom, Jr. |
| 5,527,311 A | 6/1996 | Procter et al. |
| 5,531,746 A | 7/1996 | Errico et al. |
| 5,534,032 A | 7/1996 | Hodorek |
| 5,549,612 A | 8/1996 | Yapp et al. |
| 5,569,247 A | 10/1996 | Morrison |
| 5,569,251 A | 10/1996 | Baker et al. |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,607,428 A | 3/1997 | Lin |
| 5,616,142 A | 4/1997 | Yuan et al. |
| 5,616,144 A | 4/1997 | Yapp et al. |
| 5,620,443 A | 4/1997 | Gertzbein et al. |
| 5,643,265 A | 7/1997 | Errico et al. |
| 5,653,708 A | 8/1997 | Howland |
| 5,676,666 A | 10/1997 | Oxland et al. |
| 5,676,703 A | 10/1997 | Gelbard |
| 5,681,311 A | 10/1997 | Foley et al. |
| 5,681,312 A | 10/1997 | Yuan et al. |
| 5,709,686 A | 1/1998 | Talos et al. |
| 5,713,900 A | 2/1998 | Benzel et al. |
| 5,725,588 A | 3/1998 | Errico et al. |
| 5,728,127 A | 3/1998 | Asher et al. |
| 5,735,853 A | 4/1998 | Olerud |
| 5,735,899 A | 4/1998 | Schwartz et al. |
| 5,741,258 A | 4/1998 | Klaue et al. |
| 5,797,912 A | 8/1998 | Runciman et al. |
| 5,810,823 A | 9/1998 | Klaue et al. |
| 5,876,402 A | 3/1999 | Errico et al. |
| 5,879,389 A | 3/1999 | Koshino |
| 5,904,683 A | 5/1999 | Pohndorf et al. |
| 5,951,558 A | 9/1999 | Fiz |
| 5,954,722 A | 9/1999 | Bono |
| 5,964,762 A | 10/1999 | Biedermann et al. |
| 5,976,141 A | 11/1999 | Haag et al. |
| 6,017,345 A | 1/2000 | Richelsoph |
| 6,022,350 A | 2/2000 | Ganem |
| 6,030,389 A | 2/2000 | Wagner et al. |
| 6,039,740 A | 3/2000 | Olerud |
| 6,106,557 A | 8/2000 | Robioneck et al. |
| 6,117,173 A | 9/2000 | Taddia et al. |
| 6,129,730 A | 10/2000 | Bono et al. |
| 6,139,550 A | 10/2000 | Michelson |
| 6,152,927 A | 11/2000 | Farris et al. |
| 6,159,213 A | 12/2000 | Rogozinski |
| 6,193,721 B1 | 2/2001 | Michelson |
| 6,206,882 B1 | 3/2001 | Cohen |
| 6,214,005 B1 | 4/2001 | Benzel et al. |
| 6,224,602 B1 | 5/2001 | Hayes |
| 6,228,085 B1 | 5/2001 | Theken et al. |
| 6,235,033 B1 | 5/2001 | Brace et al. |
| 6,235,034 B1 | 5/2001 | Bray |
| 6,238,396 B1 | 5/2001 | Lombardo |
| 6,241,731 B1 | 6/2001 | Fiz |
| 6,254,603 B1 | 7/2001 | Gertzbein et al. |
| 6,258,089 B1 | 7/2001 | Campbell et al. |
| 6,261,291 B1 | 7/2001 | Talaber et al. |
| 6,273,889 B1 | 8/2001 | Richelsoph |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,322,562 B1 | 11/2001 | Wolter |
| 6,328,738 B1 | 12/2001 | Suddaby |
| 6,331,179 B1 | 12/2001 | Freid et al. |
| 6,332,887 B1 | 12/2001 | Knox |
| 6,342,055 B1 | 1/2002 | Eisermann et al. |
| 6,361,537 B1 | 3/2002 | Anderson |
| 6,364,881 B1 | 4/2002 | Apgar et al. |
| 6,383,186 B1 | 5/2002 | Michelson |
| 6,398,783 B1 | 6/2002 | Michelson |
| 6,402,755 B1 | 6/2002 | Pisharodi |
| 6,402,756 B1 | 6/2002 | Ralph et al. |
| 6,406,478 B1 | 6/2002 | Kuo |
| 6,413,259 B1 | 7/2002 | Lyons et al. |
| 6,416,528 B1 | 7/2002 | Michelson |
| 6,428,542 B1 | 8/2002 | Michelson |
| 6,454,769 B2 | 9/2002 | Wagner et al. |
| 6,454,771 B1 | 9/2002 | Michelson |
| 6,458,133 B1 | 10/2002 | Lin |
| 6,478,797 B1 | 11/2002 | Paul |
| 6,503,250 B2 | 1/2003 | Paul |
| 6,527,776 B1 | 3/2003 | Michelson |
| 6,533,786 B1 | 3/2003 | Needham et al. |
| 6,572,619 B2 | 6/2003 | Santilli |
| 6,575,975 B2 | 6/2003 | Brace et al. |
| 6,579,290 B1 | 6/2003 | Hardcastle et al. |
| 6,592,586 B1 | 7/2003 | Michelson |
| 6,595,993 B2 | 7/2003 | Donno et al. |
| 6,599,290 B2 | 7/2003 | Bailey et al. |
| 6,602,255 B1 | 8/2003 | Campbell et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,652,525 B1 | 11/2003 | Assaker et al. |
| 6,669,700 B1 | 12/2003 | Farris et al. |
| 6,679,883 B2 | 1/2004 | Hawkes et al. |
| 6,692,503 B2 | 2/2004 | Foley et al. |
| 6,695,846 B2 | 2/2004 | Richelsoph et al. |
| 6,755,833 B1 | 6/2004 | Paul et al. |
| 6,761,719 B2 | 7/2004 | Justis et al. |
| 6,855,147 B2 | 2/2005 | Harrington, Jr. |
| 7,008,427 B2 | 3/2006 | Sevrain |
| 2001/0014807 A1 | 8/2001 | Wagner et al. |
| 2001/0021851 A1 | 9/2001 | Eberlein et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0013586 A1 | 1/2002 | Justis et al. |
| 2002/0022843 A1 | 2/2002 | Michelson |
| 2002/0045896 A1 | 4/2002 | Michelson |
| 2002/0045898 A1 | 4/2002 | Freid et al. |
| 2002/0045899 A1 | 4/2002 | Errico et al. |
| 2002/0049444 A1 | 4/2002 | Knox |
| 2002/0058939 A1 | 5/2002 | Wagner et al. |
| 2002/0065517 A1 | 5/2002 | Paul |
| 2002/0068938 A1 | 6/2002 | Jackson |
| 2002/0077630 A1 | 6/2002 | Lin |
| 2002/0111630 A1 | 8/2002 | Ralph et al. |
| 2002/0120268 A1 | 8/2002 | Berger |
| 2002/0120271 A1 | 8/2002 | Dixon et al. |
| 2002/0120272 A1 | 8/2002 | Yuan et al. |
| 2002/0120273 A1 | 8/2002 | Needham et al. |
| 2002/0128654 A1 | 9/2002 | Steger et al. |
| 2002/0128655 A1 | 9/2002 | Michelson |
| 2002/0151893 A1 | 10/2002 | Santilli |
| 2002/0151899 A1 | 10/2002 | Bailey et al. |

| | | |
|---|---|---|
| 2002/0173790 A1 | 11/2002 | Chang et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023242 A1 | 1/2003 | Harrington, Jr. |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0078583 A1 | 4/2003 | Biedermann et al. |
| 2003/0083658 A1 | 5/2003 | Hawkes et al. |
| 2003/0093082 A1 | 5/2003 | Campbell et al. |
| 2003/0105462 A1 | 6/2003 | Haider |
| 2003/0130661 A1 | 7/2003 | Osman |
| 2003/0135216 A1 | 7/2003 | Sevrain |
| 2003/0149434 A1 | 8/2003 | Paul |
| 2003/0153920 A1 | 8/2003 | Ralph et al. |
| 2003/0181912 A1 | 9/2003 | Michelson |
| 2003/0187440 A1 | 10/2003 | Richelsoph et al. |
| 2003/0187441 A1 | 10/2003 | Bolger et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0225409 A1 | 12/2003 | Freid et al. |
| 2004/0030338 A1 | 2/2004 | Paul |
| 2004/0087951 A1 | 5/2004 | Khalili |
| 2004/0092939 A1 | 5/2004 | Freid et al. |
| 2004/0097934 A1 | 5/2004 | Farris et al. |
| 2004/0097935 A1 | 5/2004 | Richelsoph et al. |
| 2004/0097950 A1 | 5/2004 | Foley et al. |
| 2004/0122426 A1 | 6/2004 | Michelson |
| 2004/0127896 A1 | 7/2004 | Lombardo et al. |
| 2004/0127899 A1 | 7/2004 | Konieczynski et al. |
| 2004/0204710 A1 | 10/2004 | Patel et al. |
| 2004/0220571 A1 | 11/2004 | Assaker et al. |
| 2005/0038436 A1 | 2/2005 | Michelson |
| 2005/0049593 A1 | 3/2005 | Duong et al. |
| 2005/0192577 A1 | 9/2005 | Mosca et al. |
| 2005/0283152 A1 | 12/2005 | Lindemann et al. |
| 2007/0123879 A1 | 5/2007 | Songer et al. |

FOREIGN PATENT DOCUMENTS

| | | |
|---|---|---|
| DE | 28 08 971 | 9/1979 |
| DE | 44 09 833 | 10/1995 |
| EP | 0 455 255 | 11/1991 |
| EP | 0 903 113 | 3/1999 |
| EP | 0 988 833 | 3/2000 |
| EP | 0 995 404 | 4/2000 |
| EP | 1 106 144 | 6/2001 |
| EP | 1 285 632 | 2/2003 |
| EP | 1 336 383 | 8/2003 |
| EP | 1 364 623 | 11/2003 |
| FR | 1505513 | 12/1967 |
| FR | 2435243 | 4/1980 |
| FR | 2556583 | 6/1985 |
| FR | 2740321 | 4/1997 |
| FR | 2836369 | 8/2003 |
| SU | 1424824 | 9/1988 |
| WO | 88/03781 | 6/1988 |
| WO | 91/03994 | 4/1991 |
| WO | 95/31941 | 11/1995 |
| WO | 97/22306 | 6/1997 |
| WO | 00/24325 | 5/2000 |
| WO | 00/66011 | 11/2000 |
| WO | 00/78238 | 12/2000 |
| WO | 01/26567 | 4/2001 |
| WO | 02/076317 | 10/2002 |
| WO | 02/080789 | 10/2002 |
| WO | 03/007826 | 1/2003 |
| WO | 03/071966 | 9/2003 |

OTHER PUBLICATIONS

Synthes Spine, CSLP Variable Angle for Use with the Cervical Spine Locking Plate System, Technique Guide, 28 pages.
Thomas A. Zdeblick, M.D. and Harry N. Herkowitz, M.D., Medtronic Sofamor Danek, Premier Anterior Cervical Plate System, Surgical Technique, Copyright 2000, 30 pages.
Tara Parker-Pope, New Procedure Makes Spinal-Fusion Surgery Less Taxing on Patient, Health Journal, reprinted from The Wall Street Journal, Friday, Jan. 5, 2011, 1 page, Journal Reprints, Princeton, N.J.
Interpore Cross International, Any Way You Place It, C-TEK Spells Cervical Technology, product literature, Copyright 2001, 1 page.
Interpore Cross International, C-TEK Anterior Cervical Plate System, product literature, Oct. 2000, 1 page.
Endius, Inc., Window Cervical Stabilization System, product literature, Copyright 2000, 10 pages.
Aesculap, Caspar Instruments for Anterior Cervical Fusion, product literature, 4 pages.
NDC Nitinol Devices & Components, screen shots of website www.nitinol.com, 3 pages.
Special Metal Corporation, Nitinol, Superelastic Ni-Ti alloy, website, www.specialmetals.com/products/data_nitinol.htm, printed Dec. 5, 2001, 4 pages.
Aesculap, Advanced Biomechanical Concept, product literature, 11 pages.
Eurosurgical, Oria Zenith Specifications, product literature, Mar. 2003, 18 pages.
Eurosurgical, Zenith the perfect alliance for successful cervical fusions, website, www.eurosurgical.com/Zenith.html, printed Apr. 15, 2003, 2 pages.
Cross Medical, The Market for Spinal Implants, website, www.crossmedical.com/spinal.html, printed May 7, 2001, 4 pages.
T. A. Zdeblick, M.D. and H. N. Herkowitz, M.D., Premier Cervical Plate System, Slides from presentation, Nov. 2000, pp. 1-5 and 7-8, Kohler, Wisconsin.

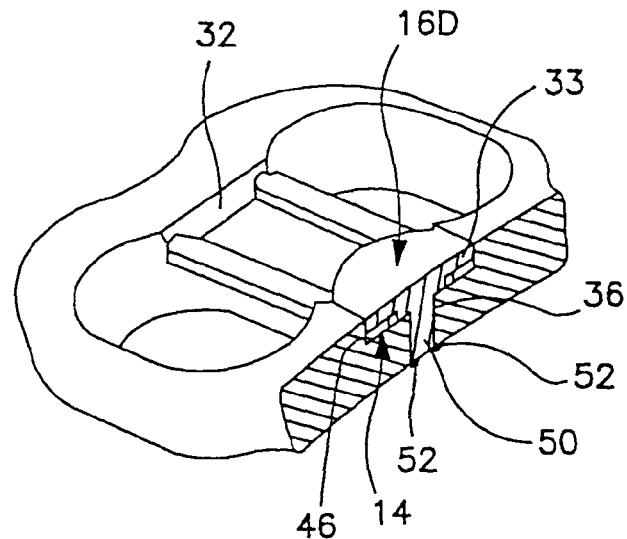
FIG. 13
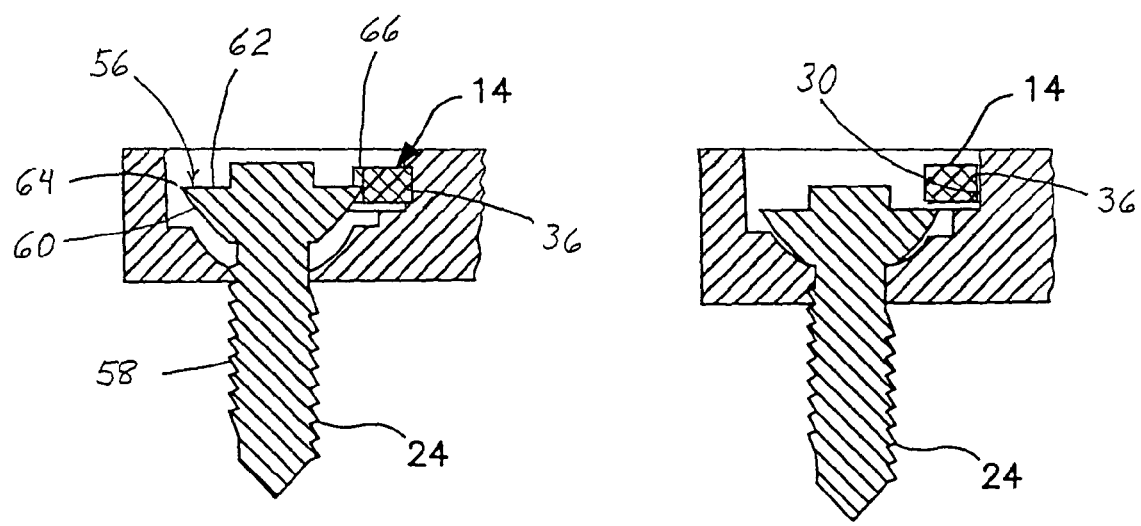
FIG. 5AFIG. 5B

SPINAL PLATE ASSEMBLY

CROSS REFERENCE TO RELATED APPLICATIONS

This application claims priority under 35 U.S.C. §120 to application Ser. No. 10/627,137 filed Jul. 24, 2003, application Ser. No. 10/202,705 filed Jul. 24, 2002 and application Ser. No. 10/014,409 filed Dec. 14, 2001, all the above of which are incorporated herein by reference in their entireties.

BACKGROUND

The present invention relates to devices for the fixation and/or support of bones. In particular, the present invention relates to a spinal plate assembly, and a corresponding spinal plate, for the fixation and/or support of bones of the spinal column. The plate of the present invention has particular application in situations where compressional or settling forces, as well as torsional and flexing forces, of "fixed" vertebrae on a spinal plate cause significant stressing and potential failure of the spinal plate and/or plate components.

Vertebral fixation has become a common approach to treating spinal disorders and fractures, and for fusion of vertebrae at the time such fixation is instituted. Namely, one or more vertebrae are fixed in position relative to one or more other vertebrae above and/or below the vertebrae to be fixed. Generally, a spinal plate is the device of choice used for mechanically supporting such vertebral fixation. A typical spinal plate includes a plate having a plurality of apertures therethrough. A plurality of fasteners, i.e., bone screws, are generally positioned into and through respective ones of the apertures of the plate to secure the spinal plate to bone, such as to two or more respective upper and lower supporting adjacent spinal vertebrae. The screws are fastened to the respective support vertebrae to thereby attach the spinal plate to the respective vertebrae. In general, such plate and screw assemblies can be utilized, for example, for anterior fixation of the spine for cervical, lumbar, and/or thoracic fixation.

The basis of anterior fixation or plating is to approach the spine from an anterior or anterio-lateral approach, and use the screws to solidly mount the spinal plate to the affected vertebrae. In addition to the application of a spinal plate, graft material may be combined in an attempt to permanently fuse together adjacent vertebrae. The graft material can consist of bone grafts obtained from bones of the recipient or another individual.

A common problem associated with the use of such spinal plates is the tendency of the bone screws to "back out" or pull away or otherwise withdraw from the bone into which they are mounted. This problem occurs, primarily, due to the normal torsional and bending motions of the body and spine. This is a particularly important problem because as the screws become loose and pull away or withdraw from the bone, the heads of the screws can rise above the surface of the spinal plate and, possibly, even work their way completely out of the bone. While this condition can cause extreme discomfort for the recipient, this condition can also create a number of potentially serious physiological problems given the significant amount of nervous and vascular structures located at or near the potential locations of anterior spinal plate fixations.

A number of plate assembly designs have been proposed in attempts to prevent screws from pulling away or withdrawing from the bone and/or to prevent the screws from backing out or pulling away or withdrawing from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments, which include potential for breakage of the screws, or which require particular precision and alignment in their application in order to work correctly. Additionally, loose components and accessories of spinal plates, which address the "backing-out" or withdrawal problem, can get dropped and/or misplaced while the vertebral fixation surgical procedure is taking place, prolonging and complicating the procedure as well as creating substantial risk of harm to the recipient.

Yet another common problem associated with the use of such spinal plates is the tendency, of the vertebrae which are being treated, to settle after the spinal plate has been installed. Such settling adds compression forces to the above-listed forces, and raises the probability that the bone screws will break, will back out, or otherwise pull away, or withdraw from the bone into which they were mounted.

It is an object of the invention to provide spinal plate assemblies which facilitate secure bone-to-bone fixation and/or support, such as at e.g. adjacent or second adjacent vertebrae, while accommodating post-procedural compression between the respective bones.

It is another object of the invention to provide spinal plate assemblies which afford substantial protection against pulling away or withdrawal of mounting components, which pulling away or withdrawal may result e.g. from torsional movement, flexing movement, or stress and/or dynamic load sharing of the vertebrae, the protection thereby enhancing the bone rebuilding process carried on by the living body.

It is yet another object of the invention to provide spinal plate assemblies which attenuate application of stress on the plate apparatus and on the affixing components.

It is a further object of the invention to provide spinal plate assemblies comprising a spinal plate and resiliently movable bands, the assemblies being so mounted and positioned as to enable bone fasteners to pass such bands, with corresponding flexing or other movement of such bands, when the bone fasteners are being installed in a recipient user and which, in combination with the designs of the bone fasteners, prevent unintended withdrawal of the bone fasteners after installation of the bone fasteners in the recipient user.

It is yet a further object of the invention to provide spinal plate assemblies which can be completely pre-assembled such that no assembly steps need be performed on the spinal plate assembly, itself, while the spinal plate assembly is being installed in a recipient user thereof.

It is still a further object of the invention to provide spinal plate assemblies wherein apparatus, in such spinal plate assemblies, for preventing withdrawal of bone fasteners from the bone, after installation of the bone fasteners in a recipient user, are automatically activated, to prevent such withdrawal, as a consequence of the installation of suitably-configured such bone fasteners.

SUMMARY

This invention provides novel spinal plate assemblies, and methods of use, wherein a retaining member such as a resiliently movable element, mounted to the spinal plate, as a consequence of driving a bone fastener through the spinal plate assembly and into bone structure of a recipient user of such spinal plate assembly, activates a blocking feature of the spinal plate assembly to thereby prevent the bone fastener from withdrawing out of the spinal plate assembly and past the resiliently movable element.

Thus, the invention comprehends a spinal plate assembly, comprising a spinal plate, the spinal plate having a length and comprising a top surface, a bottom surface opposite the top surface, the bottom surface being adapted to be positioned adjacent bone structure of a recipient user, and a plurality of bone-fastener-receiving apertures, the apertures being adapted to receive bone fasteners therethrough for mounting the spinal plate assembly to bone structure of the recipient user/patient; and a movable retaining element such as a movable retaining band, mounted to the spinal plate, the retaining element being effective, when a bone fastener is driven through an aperture into bone structure of such recipient user, as a consequence of driving the bone fastener, to activate a blocking feature of the spinal plate assembly. The blocking feature inhibits the bone fastener from withdrawing out of the spinal plate assembly and past the retaining element.

In some embodiments, the retaining element is a retaining band which extends between first and second ones of the bone-fastener-receiving apertures and extends into the first and second ones of the bone-fastener-receiving apertures.

In some embodiments, such band or other retaining element band comprises a plastic composition which is safe for use in living human or animal bodies as an implantable plastic, and which band has suitable strength, rigidity, and deflection properties to perform the desired functions in an anticipated use environment, such as for example and without limitation, one or more materials selected from the group consisting of polyetherimide copolymer, acetal copolymer, polyethersulfone, polyarylethersulfone, polycarbonate, ultra high molecular weight polyethylene, polyetheretherketone, and polyaryletherketone, and blends and mixtures of these materials.

Preferred plastic composition of the band or other retaining element comprises at least one of polyetheretherketone and polyaryletherketone.

In some embodiments, the retaining element comprises a resiliently movable band, a length of the band extending alongside, and extending across a portion of, one or more corresponding ones of the apertures, composition and structure of the resiliently movable band being adapted such that, as a bone fastener is driven alongside and past the movable band, the movable band can respond to transverse urging of the bone fastener, thereby to move transversely of the length of the band, from a first position, until a control structure on the bone fastener is driven past the band, whereupon the band can return to the first position and overlie the control structure of the so-driven bone fastener and thereby prevent the bone fastener from withdrawing.

In some embodiments, the retaining element comprises a resiliently movable band, a length of the band extending alongside and extending across a portion of, one or more corresponding ones of the bone-fastener-receiving apertures.

In some embodiments, the spinal plate further comprises a channel extending downwardly from the top surface of the spinal plate, the channel having generally opposing side walls thereof opening into and extending alongside ones of the plurality of bone-fastener-receiving apertures, the band being disposed in the channel and extending along the channel and into respective one or more of the apertures.

In some embodiments, at least all except two, and preferably all, of the bone-fastener-receiving apertures comprise slots, all of the slots having commonly oriented axes along elongate dimensions of the slots, which accommodate longitudinal movement of the bone fasteners in the slots with respect to the spinal plate after installation of the spinal plate assembly in a recipient user, thus enabling longitudinal movement of such bone fasteners in the slots, with respect to the spinal plate, after the spinal plate assembly has been installed in a recipient user.

In some embodiments, all of the bone-fastener-receiving apertures comprise slots, having lengths greater than respective widths of the slots.

In other embodiments, first and second ones of the bone-fastener-receiving apertures comprise circular openings.

In some embodiments, all the bone-fastener-receiving apertures comprise circular openings.

In some embodiments, the movable band extends along substantially the full length of the spinal plate.

Preferred embodiments include a second movable band, and the first and second movable bands extend along substantially full lengths of respective first and second sides of the channel, the first and second movable bands collectively extending along the sides of all of the bone-fastener-receiving apertures.

In some embodiments, a second movable band has a composition corresponding to the composition of the first movable band, and the first and second movable bands collectively extend along the sides of all of the bone-fastener-receiving apertures.

In some embodiments, the spinal plate assembly further comprises a band retainer, optionally more than one band retainer, mounting the flexible band or other retaining element to the spinal plate, optionally at loci away from the bone-fastener-receiving apertures.

In preferred embodiments, the movable bands are properly positioned with respect to the apertures so as to let control structure on the bone fastener pass below a respective movable band, with resilient movement of the movable band, and without exceeding a flexural limit of the movable band, such that the movable band returns to a blocking position over the bone fastener after the control structure on the bone fastener passes below the respective movable band.

In preferred embodiments, the spinal plate is elongate, the bone-fastener-receiving apertures are arrayed in first and second rows along a length of the spinal plate, the spinal plate assembly further comprising a second resiliently flexible band, wherein the first and second resiliently flexible bands are mounted at the opposing side walls of the channel, and extend along a portion of the length of the channel occupied by the bone-fastener-receiving apertures.

In some embodiments, the retaining element comprises a resiliently flexible band, a portion of a length of the band being positioned alongside, and extending across a portion of, one or more of the apertures.

Some embodiments of the invention include an intermittent channel extending along the length of the spinal plate, and intermittently expressed adjacent the apertures, the channel optionally extending downwardly from the top surface of the spinal plate, optionally further comprising retainer structure mounting the resiliently flexible band in the spinal plate assembly.

In preferred embodiments, the retainer structure is comprised in, and is an integral part of, the spinal plate.

In other embodiments, the retainer structure comprises one or more distinct retainer elements.

In some embodiments, the resiliently movable band is under constant flexural stress.

BRIEF DESCRIPTION OF THE DRAWINGS

FIG. 5A is a cross-section as in FIG. 5, but at a 90 degree angle from the cross-section of FIG. 5, thus looking along the length of the spinal plate, and showing the resiliently flexible band flexed by passage of the head of a bone screw.

FIG. 5B is a cross-section as in FIG. 5A wherein the head of the bone screw has passed the bottom of the flexible band thus to enable the resiliently flexible band to revert to its unflexed condition over the head of the bone screw.

FIG. 13 is a cross-section of the spinal plate assembly of FIG. 11, taken at 13-13 of FIG. 11.

Figure 2:
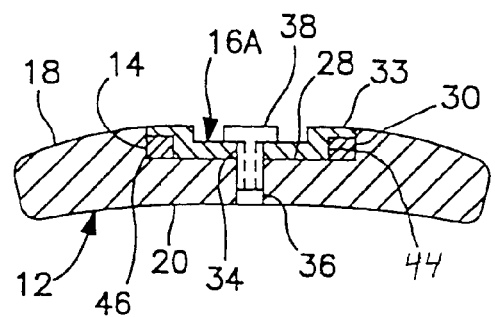
FIG. 2 shows a cross-section of the spinal plate assembly of FIG. 1, taken at 2-2 of FIG. 1.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1:
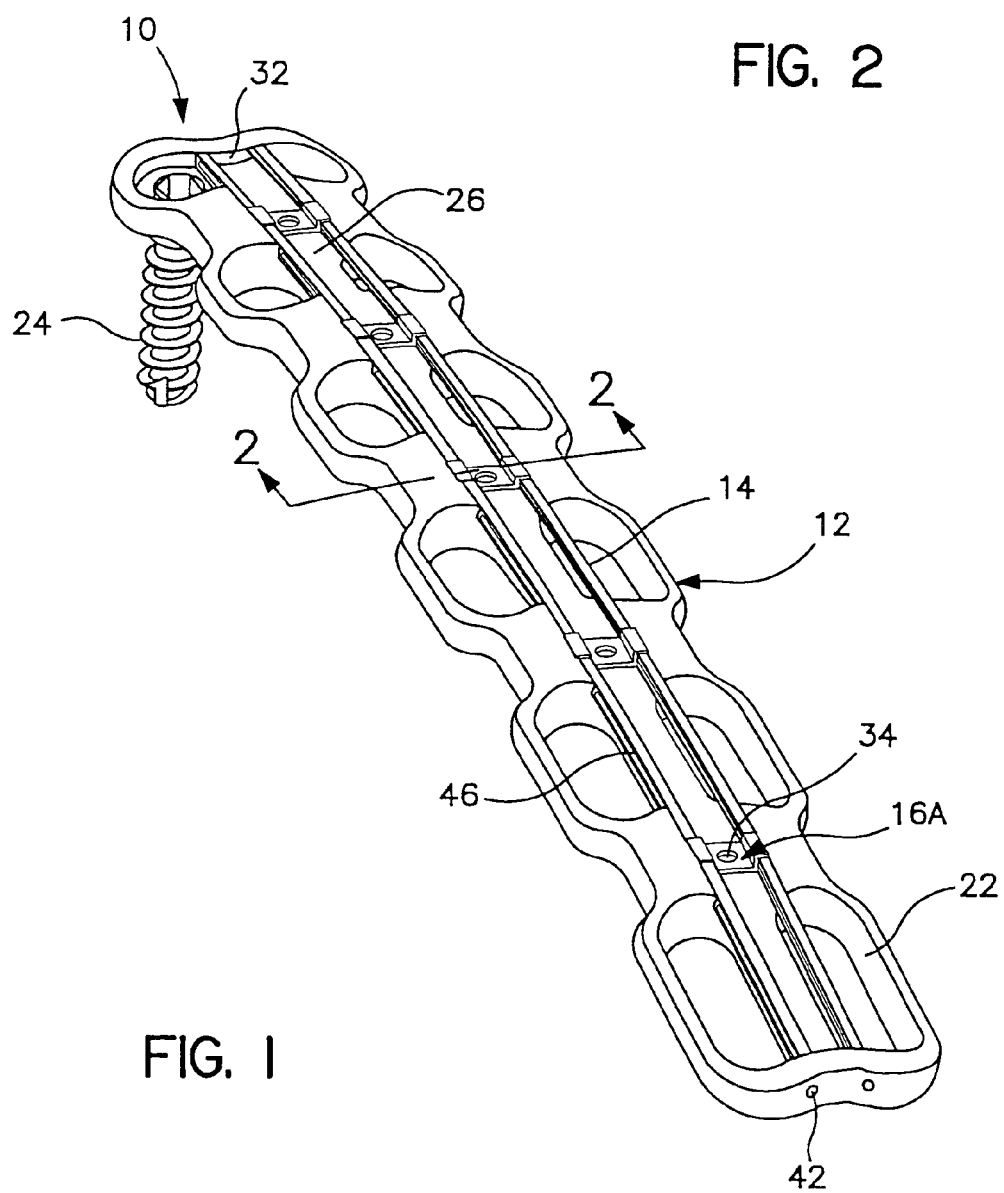
FIG. 1 shows a pictorial view of a first embodiment of spinal plate assemblies of the invention.
Figure 3:
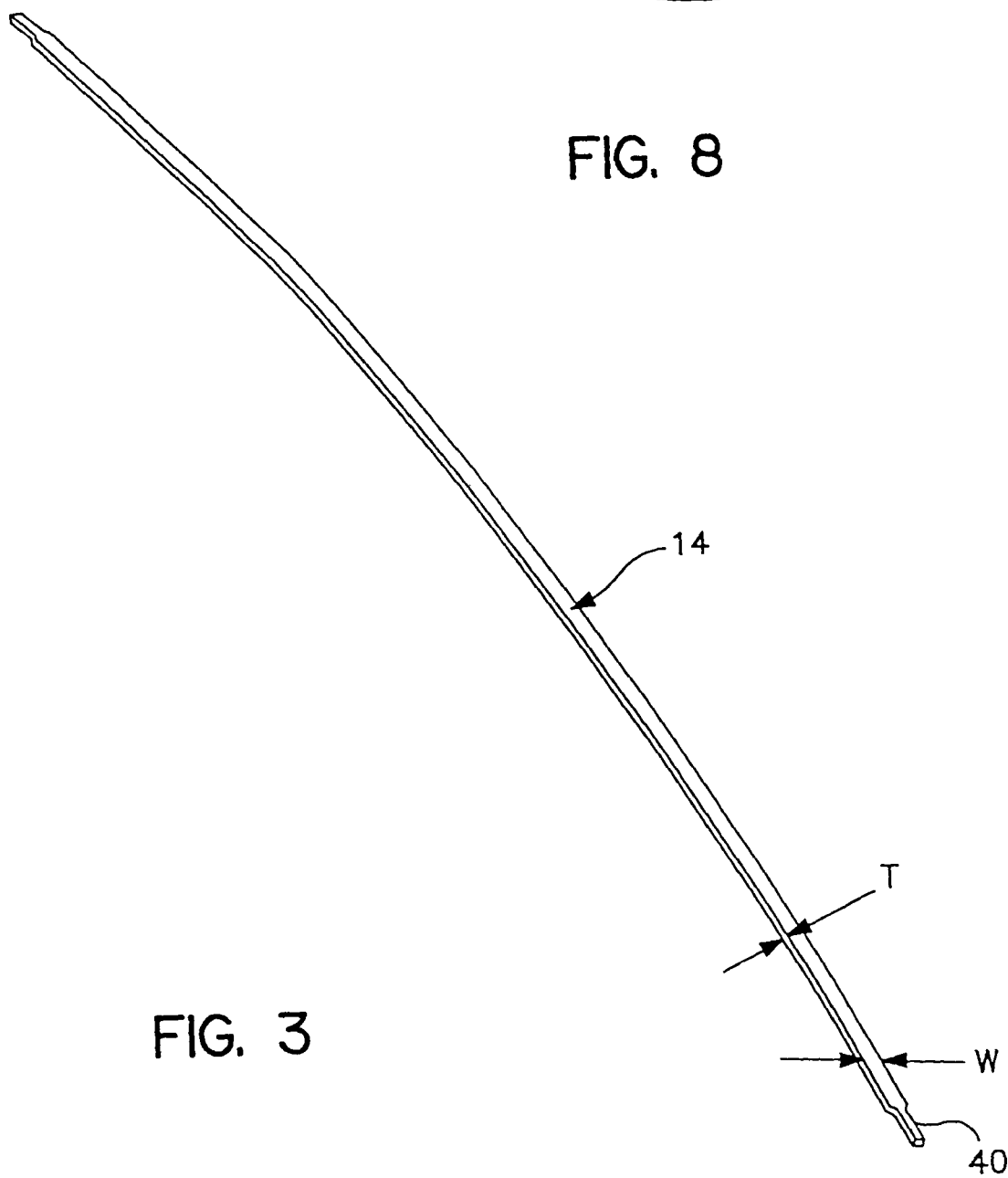
FIG. 3 shows a pictorial view of a flexible band which can be used in spinal plate assemblies of the invention.

Referring now to the embodiments represented by FIGS. 1-3, a spinal plate assembly 10 of the invention includes a spinal plate 12, first and second retaining bands or blocking members 14, and a plurality of band retainers 16A.

Spinal plate 12 has a top surface 18, a bottom surface 20 adapted to be positioned adjacent bone structure of a recipient user of the spinal plate assembly, and a plurality of bone-fastener-receiving apertures 22 which receive bone fasteners such as bone screws 24. Apertures 22 are arranged in first and second rows of such apertures, along the length of the plate.

Figure 9:
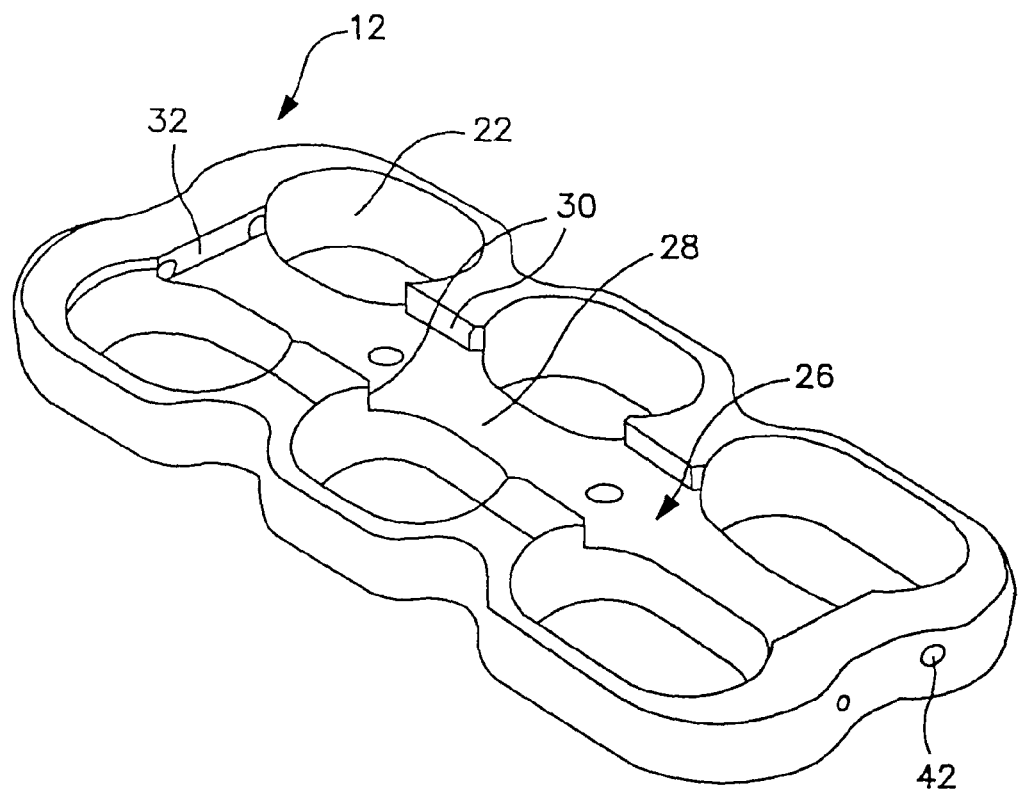
FIG. 9 shows a pictorial view of a spinal plate used in a fourth embodiment of spinal plate assemblies of the invention.

Top surface 18 of the spinal plate defines a channel 26 extending along the length of the support plate. As best seen in FIG. 9, channel 26 has a bottom wall 28, opposing side walls 30, and opposing end walls 32.

Returning now to the embodiments specifically represented by FIGS. 1 and 2, a given retainer 16A has a pair of opposing flanges 33, each of which extends over one of the retaining bands 14 at a location displaced from respective adjacent apertures 22, whereby the respective band is trapped between the bottom surface 28 of the channel, the respective side surface of the channel, and the respective flange 33 of the retainer. Each retainer 16A includes an aperture 34. An aperture 36 in the spinal plate underlies aperture 34 in each such retainer 16A. A locking screw 38 extends through aperture 34 and into aperture 36, securing retainer 16A to the spinal plate. Preferably, the retainer is sized and configured, in combination with the side and bottom walls of the channel, and the configurations of the bands, to apply substantial e.g. side and/or top loading pressure against the bands thereby to effectively prevent movement of the bands with respect to the spinal plate at the location of the retainer.

Bands 14 have reduced cross-section ends 40. End walls 32 of the spinal plate include apertures 42 for receiving the reduced cross-section ends 40 of the bands. Band ends 40 are accordingly received in apertures 42, thereby restraining the bands against longitudinal movement in the spinal plate assembly, as well as restraining the bands against transverse lateral movement at the end walls.

While bands 14 are effectively prevented from moving laterally at retainers 16A, and are prevented from moving laterally at end walls 32, as well as being prevented from moving longitudinally at end walls 32, the compositions of bands 14 can be selected such that the band material, itself, has a great degree of resilient flexural capacity. Accordingly, at locations displaced from such restraint as applied at band retainers 16A and end apertures 42, e.g. at apertures 22, the bands can preferably readily flex in directions transverse to the lengths of the bands. Thus, in response to respective forces, portions of bands 14 which are relatively displaced from band retainers 16A and end apertures 42 can be moved along the width of plate 12, or upwardly from the plate. Such movement is, of course, limited by the restraints imposed periodically along the lengths of the bands by band retainers 16A and end apertures 42

Side walls 30 of the channel are specifically located and configured so as to open into the sides of, and extend along and inwardly of, the sides of apertures 22.

In general, imaginary extensions of side walls 30 project across apertures 22 at locations displaced inwardly of the aperture side walls by about 1 mm. Retainers 16A are so sized and configured that, when the retainers are installed, end surfaces 44 of the retainers abut the bands with sufficient close tolerance fit that the end surfaces 44 urge the bands solidly against the side walls of the channels. Thus, band retainers 16A position bands 14 solidly against the side walls of the channels where the band retainers interface with the bands, and typically not where the bands are passing over apertures 22. With the bands solidly against the side walls of the channel, the outwardly-disposed sides 46 of the bands are in surface-to-surface contact with side walls 30 of the channels. The outwardly-disposed sides 46 of the bands, the respective rows of apertures 22, and retainers 16A, are thus correspondingly cooperatively sized, arranged and configured with respect to each other such that, when bands 14 are trapped between the channel side walls, the channel bottom, and the retainers, the bands, when not deflected by the bone screws, extend along a path wherein the outwardly-disposed sides 46 of the bands extend closely beside the side walls 30 of the channel. Since imaginary extensions of the side walls are displaced inwardly, into the apertures, of the aperture side walls by about 1 mm, the outwardly-disposed side walls of the bands also are displaced inwardly, into the apertures, of the aperture side walls by about 1 mm.

Figures 4, 5:
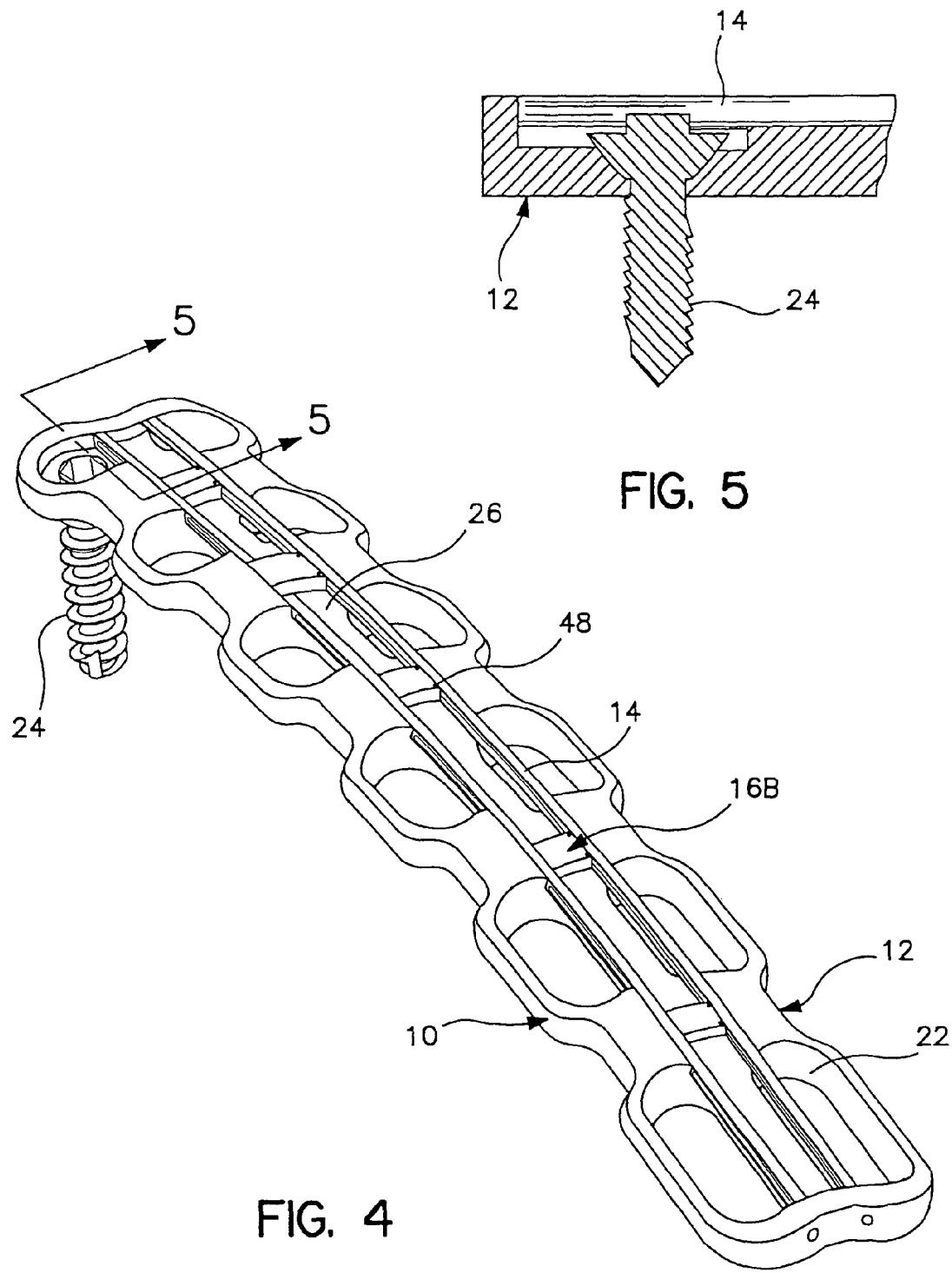
FIG. 4 shows a pictorial view of a second embodiment of spinal plate assemblies of the invention.
FIG. 5 shows a cross-section of the spinal plate assembly of FIG. 4, taken at 5-5 of FIG. 4.

FIGS. 4 and 5 illustrate a second family of embodiments of the invention. In these embodiments, all elements of the invention are the same as in the embodiments of FIGS. 1 and 2, except for the retainer and its interactions. While retainer 16A in FIGS. 1 and 2 is held in place with a locking screw 38, and has flanges 33 interfacing with the tops of bands 14, in the embodiments of FIGS. 4 and 5, retainers 16B are disposed in abutting relationship with bands 14, and are spot welded at welds 48 to bands 14. Further, retainers 16B preferably, but not necessarily, have studs (not shown in FIGS. 4-5) which extend through respective apertures corresponding to apertures 36 in plate 12 of FIGS. 1 and 2. Studs (not shown in FIGS. 4-5) can extend through the plate apertures and can be spot welded to the plate at the bottom wall of the plate. Such apertures, studs, and spot welds are shown in e.g. FIGS. 6 and 7, discussed following.

Thus, the retainers of FIGS. 4 and 5 interact with the bands through the abutment interface in combination with the spot welds between the bands and the retainers, and use the abutment interface, in combination with close fit tolerances, to urge the bands into frictional engagement with the side walls of the channel, and do not extend over the bands, themselves.

FIGS. 5, 5A, and 5B illustrate the process by which a band 14 is flexed or is otherwise caused to move when a bone screw 24 passes the band, and further illustrate the interference in a withdrawal path of the screw, provided by the band after the screw has been driven past the band and the band has returned to the less flexed or unflexed condition.

Turning especially to FIG. 5A, bone screw 24 has a head 56 and a shank 58. Head 56 has a tapered, or beveled, or conical lower surface 60, and a generally flat or concave upper surface 62 adjacent the outer edge 64 of the head. By generally flat upper surface is meant that the upper surface is generally perpendicular to a central longitudinal axis of shank 58.

As screw 24 is installed by turning the screw and thus advancing the screw into bone tissue of the recipient, and through one of the bone screw apertures, the angled lower surface 60 of the screw head approaches and pushes against band 14 at the top inner edge 66 of the band. As lower surface 60 is progressively advanced downwardly as a consequence of advancing the screw into the bone, and against band 14, the tapered angle of the lower surface of the head of the bone screw applies a transverse, side-loading force on band 14, urging the band to move away from the longitudinal axis of shank 58. As illustrated in FIG. 5A, the band can move at the locus of engagement with the lower surface of the screw head, thus to enable further driving of the screw, and further temporary displacement of the band, by continuing downward movement of the screw head. As soon as the top outer edge 64 of the head passes below band 14, the band moves back over head 56 as shown in FIG. 5B. Thus, the band serves as a safety device preventing withdrawal of the bone screw from the bone, and from the spinal plate assembly.

Figure 8:
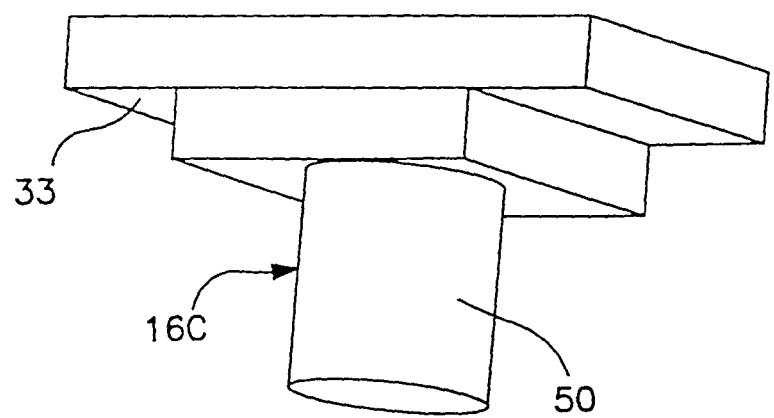
FIG. 8 shows a pictorial view of a retainer used in the spinal plate assembly illustrated in FIG. 6.
Figure 7:
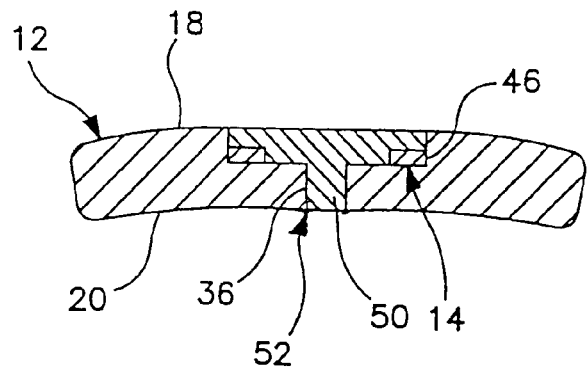
FIG. 7 shows a cross-section of the spinal plate assembly of FIG. 6, taken at 7-7 of FIG. 6.
Figure 6:
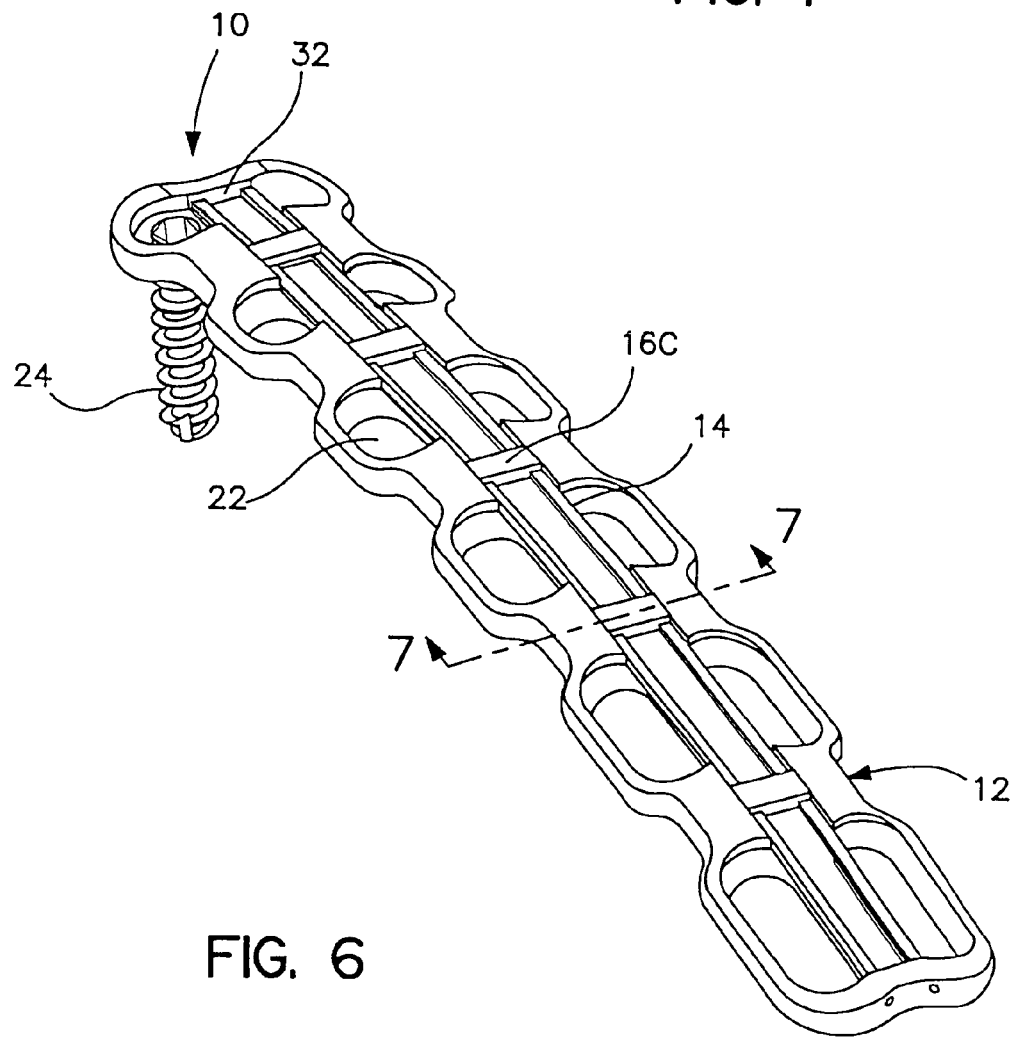
FIG. 6 shows a pictorial view of a third embodiment of spinal plate assemblies of the invention.

FIGS. 6-8 illustrate a third family of embodiments of the invention. In the embodiments of FIGS. 6-8, all elements of the invention are the same as in the embodiments of FIGS. 1-5, except for the retainer and its interactions. Retainer 16A in FIGS. 1 and 2 has a flange 33 which overlies bands 14, and is secured to plate 12 with a locking screw 38. Retainer 16B in FIGS. 4 and 5 interacts with bands 14 by abutment, fortified by spot welds to bands 14, and is secured to plate 12 with spot welds. In the family of embodiments represented by FIGS. 6-8, retainer 16C has flanges 33 (best illustrated in FIG. 8) which overlie bands 14 as in FIGS. 1 and 2 and has a stud 50 extending through aperture 36 in plate 12, as discussed with respect to FIGS. 4 and 5. Stud 36 is spot welded to plate 12 by welds 52 at bottom surface 20 of the plate. Accordingly, the securement to the plate is by spot welds displaced from apertures 22 and from bands 14. Interaction between bands 14 and retainer 16C is through overlying flanges 33 of the retainer, whereby the bands are not subjected to the direct thermal affects of the spot welding process.

FIGS. 9-13 illustrate a fourth family of embodiments of the invention. In the embodiments of FIGS. 9-13, all elements of the invention are the same as in the previous embodiments except for the retainer and its interactions, and the length and number of apertures, and corresponding length of plate 12. As seen therein, the plate in FIGS. 9-13 has only 3 bone screw receiving apertures 22 in each of the two rows of apertures. Retainer 16D, like retainer 16C has flanges 33 which overlie the bands. However flanges 33, seen especially in FIGS. 11 and 13, of retainers 16D have generally round configurations, and extend generally the full length of a portion of the channel side wall between respective ones of the apertures 22, while having straight-line edges at the side walls. Such increased flange footprint provides, in flange 33 of e.g. FIG. 11, controlling interaction over an increased fraction of the length of the bands between apertures 22, as compared to the previous embodiments, whereby control of transverse movement of the bands is extended to substantially the full length of that portion of the side wall which extends between adjacent ones of apertures 24. Retainer 16D has a stud 50 which extends through an aperture 36 in the plate and is spot-welded at welds 52.

Figure 10:
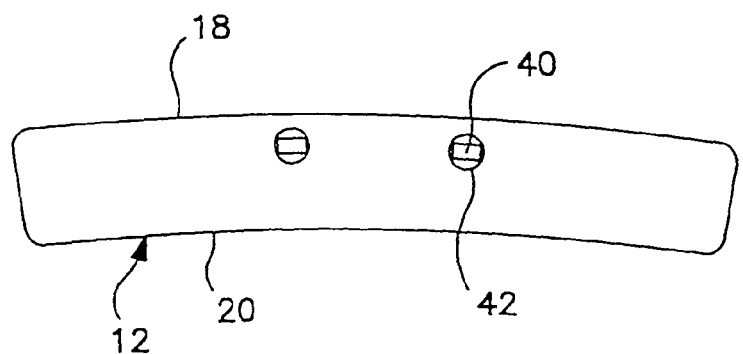
FIG. 10 is an end view of the spinal plate illustrated in FIG. 9 with bands shown installed.
Figure 11:
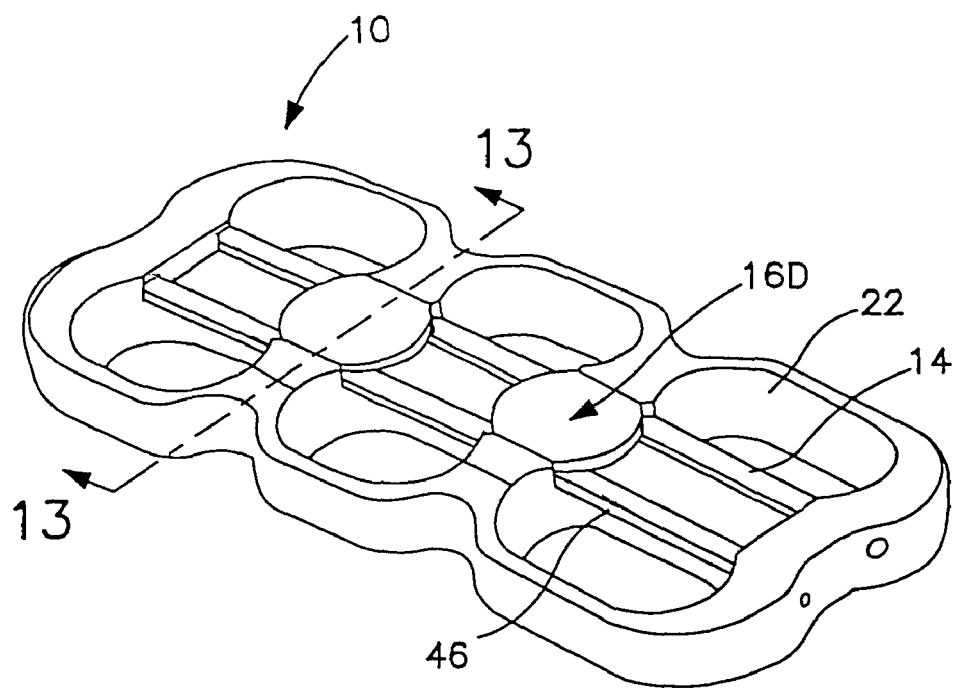
FIG. 11 shows a pictorial view of a spinal plate assembly of the invention employing the spinal plate of FIG. 9.

FIG. 10 illustrates the reduced cross-section ends 40 of bands 14 in end apertures 42, wherein the relatively larger cross-section main bodies of the bands are restrained against longitudinal movement by interaction with the inner surfaces of end walls 32.

Figure 12:
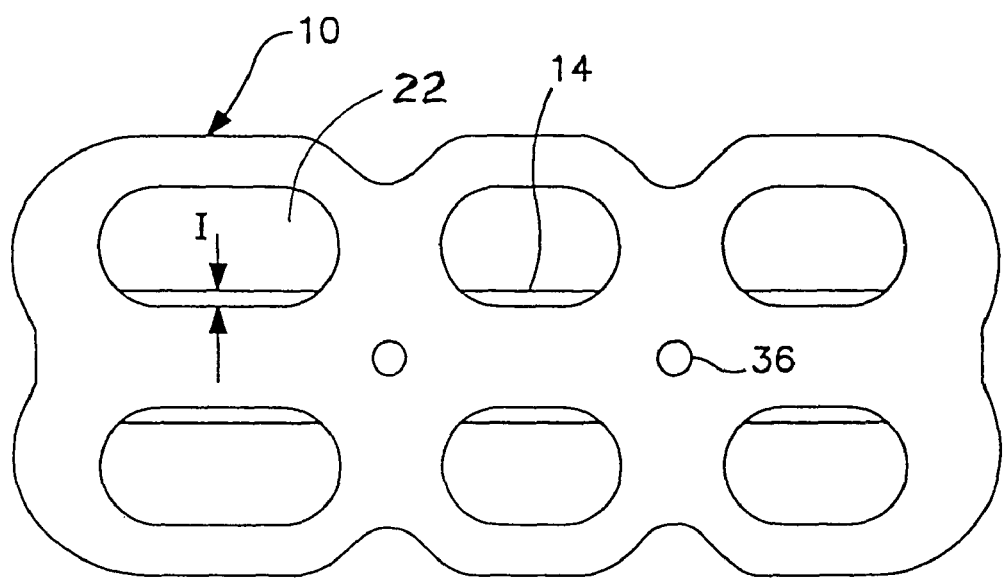
FIG. 12 shows a bottom view of the spinal plate assembly of FIG. 11, illustrating the flexible bands overlapping the open aperture area of the bone-fastener-receiving slots.

FIG. 12 illustrates a bottom view of assembly 10, directly illustrating the interference path set up by bands 14, to interfere with properly fitting bone screws, adjacent the inner edges of apertures 22. As indicated above, a preferred interference dimension "I", between the side of the aperture and the edge of the respective band, is approximately 1 mm. Such interference dimension can, of course, be different, depending on a variety of parameters relating to the specific structural and operating environments, including the relative configurations of the bone screw, the aperture, and the band. What is important is that the interference be of sufficient dimension, and that the interfering surfaces be so cooperatively configured, that the band effectively interferes with the bone screw so as to prevent the bone screw from withdrawing from assembly 12 without intentional provision for such withdrawal.

Thus, in the illustrated embodiments, the angle at which lower surface 60 of the screw head interacts with band 14 as the bone screw is being driven through plate 12 is effective to move the band sideways, out of the way of the head whereby the head can pass beyond the band. Correspondingly, the upper surface 62 of the head is so configured as to not automatically move band 14 sideways if and as the bone screw begins to back out of engagement with the bone and the plate. Rather, as the screw begins to back out, the upper surface 62 of the head comes into abutting relationship with the band, whereby band 14 serves as an automatic and effective stop, preventing the screw from backing out of the underlying bone into which the screw is screwed. Band 14 thus serves as a safety device, preventing inadvertent withdrawal of screw 24, while enabling facile installation of the screw.

Figure 14:
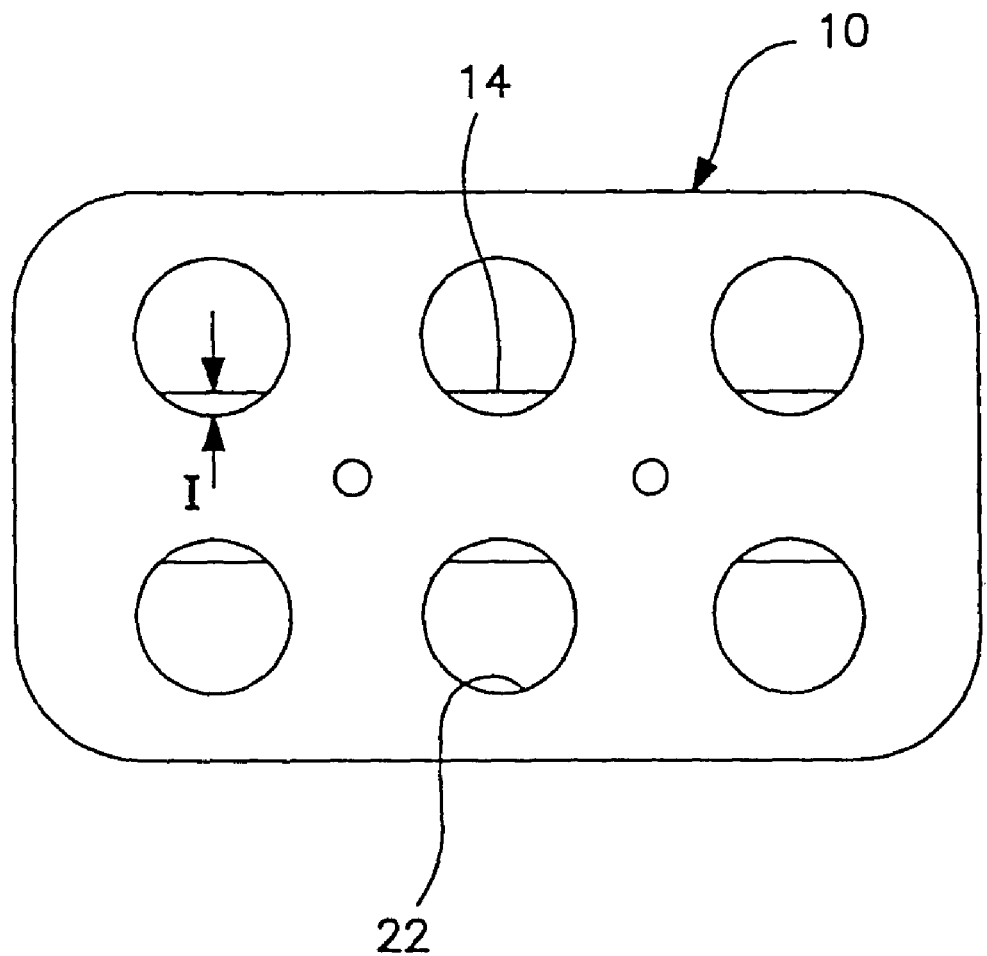
FIG. 14 shows a bottom view of a spinal plate assembly wherein all the apertures are circular.

FIG. 14 illustrates a bottom view of a fifth family of embodiments of assembly 10 wherein all of apertures 22 are circular. Such support plate assemblies have limited or no freedom of movement of the bone screws with respect to the plate, whereby the spinal plate assembly restrains movement of the bone structure to which the spinal plate assembly is mounted. Such support plate assemblies are desirable where the bone positions may be desirably fixed, and are not expected, or not desired, to move with respect to each other.

Since spinal plate assemblies of the invention are to be used within living bodies, all materials used in the spinal plate assemblies must be compatible with, and safe for use inside, the living body, e.g. animal bodies or the human body. In that regard, preferred material for spinal plate 12, and retainers 16A is titanium, or titanium alloy, for example titanium-aluminum alloy. A specific titanium aluminum alloy referred to in ASTM F-136 is (Ti6AL-4V).

Plate 12 has a length sufficiently long to span at least two vertebrae, and width and thickness sufficiently great to provide resistance to bending and torsion forces. Accordingly, where plate 12 is composed of one of the above referred to materials, typical dimensions are as follows. Typical length is at least 20 mm, up to as great as about 120 or more mm. Width is typically about 15 mm to about 20 mm. Nominal thickness is typically about 2 mm to about 3.5 mm. The bottom of channel 26 is typically about 0.7 mm to about 1.5 mm from the top surface of the plate. Such dimensions are, of course, exemplary only and not limiting and, given the above exemplary dimensions, those skilled in the art can vary such dimensions according to specific structure of respective plates and plate assemblies.

Compositions for bands 14 preferably have resilient, e.g. spring-like, flexural properties. Resilient flexural capability can be properties inherent in the metal composition, or can be properties which attend the cross-sectional structure designed into the width and thickness of the respective band, in combination with the metal composition. For example, materials which are not generally considered as having resilient, spring-like properties can, when fabricated into sufficiently small cross-sections, perform the desired resiliently flexural spring function. For example and without limitation, bands 14 can employ titanium compositions, titanium alloy compositions such as titanium-aluminum alloy compositions, for example the specific titanium aluminum alloy mentioned above, or other titanium alloys, or stainless steel compositions which, in sufficiently small cross-section, can exhibit the desired resilient spring-like properties. Other materials can be used as bands 36 and retainers 16 so long as such materials satisfy the above safety and performance requirements. All materials used in the plate assembly are, of course, medical grade materials.

Any of the plastic materials known to be safe for use in living human or animal bodies, as applies, as implantable plastics, and which have suitable hardness and rigidity, can be employed for fabricating bands 36. As with the metals, such materials must be both bio-stable and bio-compatible.

As such plastics, there can be mentioned, for example and without limitation, polyetherimide copolymer such as ULTEM®, acetal copolymer, polyethersulfone, also known as polyarylsulfone, such as RADEL A®,
polyarylethersulfone such as RADEL R®,
polycarbonate,
ultra high molecular weight polyethylene,
polyetheretherketone, also known as PEEK, available from Boedecker Plastics, Inc. Shiner, Tex.,
polyaryletherketone, also known as PEEK-OPTIMA®.

Such materials can be filled or unfilled, and can employ the usual additives, including processing aids, so long as the resultant composition is suitable as an implantable plastic for use in a living, e.g. human, body.

The spinal plates illustrated herein have closed-end channels 26 which are closed at end walls 32, with apertures 42 extending through the end walls of the channels. The invention also contemplates spinal plates wherein the channels extend the entire lengths of the plates, and are thus open ended channels (not shown). Where open ended channels are used, end retainers (not shown) can be employed to close off the ends of the channels. Such end retainers include end apertures corresponding to apertures 42, whereupon the combination of the open channel and the closing end retainers result in the same, or very similar, channel cross-section configuration at the ends of plate 12.

Channel 26 has a width sized so that the side walls extend into apertures 22 a distance sufficient to generate an interference between bands 14 and apertures 22 when the bands are disposed against side walls 30 and are in relatively less-flexed, or unflexed conditions. Channel 26 has a depth sufficient to accommodate the thicknesses of bands 14.

In a family of embodiments (not shown), channel 26 can be intermittent, and exist only adjacent apertures 22. In such embodiments, bands 14 are held in channel elements which extend e.g. downwardly from top surface 18 of plate 12, and which thus define the band paths. Separate retainers 16 are not needed, and the functions of the retainers can be provided by plate material at or adjacent the respective intermittent expressions of channel 26.

As a result of the structures of apertures 22, channel side walls 30, retainers 16A, 16B, 16C, or 16D, and bands 14, when a bone screw, which properly fits the apertures 22, is driven through an aperture 22, the head of the bone screw pushes against the respective band 14 as shown in FIG. 5A, and forces the band in a width-wise transverse direction away from the aperture in order that the head of the bone screw can pass the band. Since the band is preferably readily and resiliently flexible, the band flexes in response to the urging of the head of the bone screw, as shown in FIG. 5A. When the head of the bone screw passes below the bottom of the band, the band is no longer being held in the flexed condition by the screw head, and resiliently returns to the previous condition of being unflexed, thereby setting up a potential interference, of about 1 mm, between the band and the screw head, which interference is activated if and when the screw begins to back out of, or withdraw from, the bone plate.

The invention contemplates that bands 14 can be arranged in other than a rest, or straight, condition when not being forced sideways by the screw head. Thus, the bands can be under a degree of constant flexural stress, e.g. a pre-stressed condition, wherein the level of stress is changed as the head of the screw passes, and then reverts to the previous level of stress after the screw head passes.

Similarly, bands 14 can be in a non-straight, e.g. curvilinear or angled, configuration in a rest condition, and can still resiliently flex with respect to the bone screw as the bone screw is driven past the band.

If desired, some control structure other than the head of the screw can be used to activate and release the band. For example, control structure (not shown) can be designed into the screw below the head, above the head, or otherwise, for the purpose of activating the flexural and release properties of the band.

Whatever the positions of the band, whatever the control structure on the screw which interfaces with the band, once the band is released from the flexing of the respective control surface of the screw, and the band thus returns to the pre-stress flex condition, the band is positioned above, over, and in an interfering abutment position with respect to a path which some portion of the screw must traverse in order to withdraw from the spinal plate assembly. Referring to FIGS. 5 and 5B wherein the head of the screw has passed below the bottom of the band, and wherein the band has thus returned to the pre-stressed condition, the band is seen to overlie a portion of the surface of the head of the screw, such that if the screw begins to withdraw e.g. away from the plate, the head of the screw impacts the bottom of the band. As withdrawal of the screw progresses such that the screw impacts the bottom of the band, the band, being supported by respective retainers 16A, 16B, 16C, or 16D, prevents the screw from further withdrawal from the plate.

As seen in FIG. 5A, when the screw is driven through the plate, e.g. and into bone material of a recipient user of the spinal plate assembly, the force applied by the upwardly-extending angular bottom surface of the screw automatically pushes the band aside as the head of the screw impacts and passes the band. Once the head of the screw passes the band, the band automatically resiliently restores itself to the unflexed or less-flexed position over the head of the screw, illustrated in FIGS. 5 and 5B. Thus, in spinal plate assemblies of the invention, driving the bone screw, and thereby mounting the spinal plate assembly in the body of a recipient user thereof, automatically flexes the band, as a blocking member, out of the way of insertion of the bone screw, and then the blocking member/band automatically flexes to a locking, blocking position over the head or other control structure of the screw, thereby automatically activating the blocking and locking feature of the spinal plate assembly to block withdrawal of the bone screw, and thus to lock the bone screw in the assembly and retain joinder of the bone screw to the respective bone of the recipient user. Such bone screw can, of course be released for removal by manually or otherwise intentionally flexing the band away from the screw, and removing the screw while the band is thus held in the moved or flexed condition.

In preferred embodiments of the invention, all of apertures 22 are slot-shaped in that, e.g. in projection, each aperture has an elongate dimension and a shorter cross-dimension. In some embodiments, two of the apertures are relatively lesser lengths, and may be e.g. circular, thereby to serve as support apertures, and the remaining apertures are relatively greater lengths, as slots or slot-shaped, and serve as settle apertures, providing for the bone structure to settle while being held by the spinal plate. As seen in FIGS. 1 and 2, typically each aperture along the length of the spinal plate assembly is progressively longer/shorter, in a progressive pattern, than the adjacent apertures in the same row to accommodate the typically progressively increasing distance moved by respectively more upwardly-disposed ones of the vertebrae being treated by the plate assembly.

Typical length increments for adjacent apertures in a given row are about 1 mm. Accordingly, in a plate 12 as in FIG. 11, having three apertures per row, the length differential between the longest and shortest apertures 22 can be, for example, about 2 mm. Correspondingly, in a plate 12 as in FIG. 1 having six apertures per row, the length differential between the longest and shortest apertures 22 can be, for example, about 5 mm. The exact and actual length differentials can be somewhat different, depending on the specific use contemplated for the respective plate 12.

Typically, spinal plate assemblies of the invention have two rows of apertures. And while the spinal plate assemblies illustrated in the drawings show 2 rows of bone screw apertures, the invention can well be utilized with any number of rows of apertures, and any number of apertures per row.

Further to other embodiments, bands 14 are shown with each band extending the full length of channel 26. It is contemplated that bands 14 can be segmented so as to comprehend 2 or more bands extending e.g. serially along one or both of side walls 30. For example, a separate band can be used in support of the function of each or any aperture.

While plates 12 are shown having apertures 22 arrayed along the full length of the plate, the using surgeon selects the particular apertures through which bone screws can suitably be employed to mount the plate to bone structure of the recipient user. The particular apertures employed depend on the needs presented by the surgery being performed. Thus, bone screws can be employed through any number, at least 2, and up to all, of the apertures.

Where an aperture is a slot-shaped aperture, a bone screw employed through that aperture is advanced a sufficient distance to bring the control structure of the screw past the respective band, but not a sufficient distance to force the head of the screw against a side wall of the aperture, such as by a friction lock. With the screw head thus unsecured to the aperture walls, the screw is free to move with respect to the plate as the bones, into which the screws have been inserted, move and settle with respect to each other.

Where slot-shaped apertures are used to enable post-procedure movement of the bone screws to accommodate post-procedure settling of vertebrae in a recipient user, all of such apertures which are to participate in such settling are arranged with common orientation of the axis of the elongate dimensions of the apertures so as to reduce the possibility that any of the bone screws might frictionally bind against a side wall of the aperture while in the process of moving so as to accommodate such settling. Namely, the bone screws do not, cannot, frictionally bind in the slot-shaped apertures, as such binding would obviate any objective of accommodating sliding of the bone screws in apertures 22.

Where apertures 22 are round, whereby no sliding of the bone screws is contemplated, the screw heads can be frictionally bound to plate 22 if desired.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:
1. A spinal plate assembly, comprising:
   (a) a spinal plate, said spinal plate having a length, and an exterior side wall extending along the length of said spinal plate, said spinal plate comprising
       (i) a top surface,
       (ii) a bottom surface opposite the top surface,
       (iii) a plurality of bone-fastener-receiving apertures, and
       (iv) a channel, at least in part defining a channel opening extending downwardly, from the top surface, the channel comprising a side wall extending from the top surface toward the bottom surface, a channel bottom wall between the top surface and the bottom surface, a generally straight line portion of said channel side wall extending in a direction generally consistent with said plate exterior side wall at a location displaced from a respective said aperture;

(b) a resiliently deflectable blocker band in the channel, a length of said blocker band extending across a path traversed by a bone fastener being driven into one of the apertures.

2. A spinal plate assembly as in claim 1, said blocker band comprising a resiliently flexible band, a length of said blocker band extending across a portion of a such bone-fastener-receiving aperture.

3. A spinal plate assembly as in claim 2 wherein composition of said spinal plate comprises at least one of titanium, titanium alloy, or stainless steel.

4. A spinal plate assembly as in claim 1, the channel extending, from a location away from a respective such aperture, to such aperture.

5. A spinal plate assembly as in claim 1, further comprising a band retainer engaging said blocker band so as to assist in retaining said blocker band in the channel while accommodating limited movement of said blocker band.

6. A spinal plate assembly as in claim 1, including the channel extending intermittently along the length of said spinal plate, and thereby being intermittently expressed adjacent the apertures.

7. A spinal plate assembly as in claim 6 wherein the composition of said blocker band comprises at least one of titanium, titanium alloy, or stainless steel.

8. A spinal plate assembly as in claim 1 wherein at least all except two of said bone-fastener-receiving apertures comprise slots, having commonly oriented elongate axes enabling longitudinal movement of bone fasteners in said slots, with respect to said spinal plate after the spinal plate assembly is installed in a recipient user of said spinal plate assembly.

9. A bone support assembly, comprising:
(a) a bone support plate, said bone support plate comprising
   (i) a top surface,
   (ii) a bottom surface opposite the top surface,
   (iii) a plurality of bone-fastener-receiving apertures, and
   (iv) a channel defined in and as part of the top surface of said bone support plate, the channel having a channel side wall and a channel bottom wall, said channel side wall defining, at least in part, a channel opening extending from the top surface, to a lower end of said side wall disposed between the top surface and the bottom surface, said bottom wall extending away from a first portion of said side wall of the channel and across the channel between the top surface and the bottom surface; and
(b) a resiliently movable band in the channel, said movable band being effective, when a bone fastener is driven through a said aperture into bone structure of a recipient, to automatically and as a consequence of driving such bone fastener, activate a blocking feature of said bone support assembly effective to prevent the bone fastener from withdrawing out of said bone support assembly and past said locking member.

10. A bone support assembly as in claim 9, a channel opening extending down from the top surface, said bottom wall of the channel extending, from said side wall, across a portion of the channel opening.

11. A spinal plate assembly as in claim 9, said blocker band comprising a resiliently flexible band, a length of said blocker band extending across a portion of a such bone-fastener-receiving aperture.

12. A spinal plate assembly as in claim 9, the channel extending, from a location away from a respective such aperture, to such aperture.

13. A spinal plate assembly as in claim 9, further comprising a band retainer engaging said blocker band so as to assist in retaining said blocker band in the channel while accommodating limited movement of said blocker band.

14. A spinal plate assembly as in claim 9, including the channel extending intermittently along the length of said spinal plate, and thereby being intermittently expressed adjacent the apertures.

15. A spinal plate assembly, comprising:
(a) a spinal plate, said spinal plate comprising
   (i) a top surface,
   (ii) a bottom surface opposite the top surface,
   (iii) a plurality of bone-fastener-receiving apertures,
   (iv) a channel extending down from the top surface, along a channel side wall, to a bottom wall at a lower end of said side wall between the top surface and the bottom surface, said bottom wall extending inwardly, into the aperture, from said channel side wall, said channel side wall extending, from a location away from a given such fastener-receiving aperture, to the respective fastener-receiving aperture; and
(b) a resiliently deflectable blocking band in the channel, said blocking band extending into a respective one of the apertures, and responding, as a consequence of a bone fatener being driven through the respective aperture, to a side force applied by an interfering element of such bone fastener, by being moved away from such interfering element, and further responding by returning to a blocking position over the interfering element after such interfering element has passed said blocking band; and
(c) a band retainer engaging said blocker band so as to assist in retaining said blocker band in the channel while accommodating limited movement of said blocker band.

16. A spinal plate assembly as in claim 15, including the channel extending intermittently along the length of said spinal plate, and thereby being intermittently expressed adjacent the apertures.

17. A bone support assembly, comprising:
(a) a bone support plate, said bone support plate comprising a top surface, a bottom surface opposite the top surface, a plurality of bone-fastener-receiving apertures for receiving bone fasteners therethrough for securing said bone support assembly to bone structure of a recipient user,
said bone support plate further comprising a channel defined in and as part of the top surface of said bone support plate, the channel having a side wall thereof extending to one of said plurality of bone-fastener-receiving apertures, and a bottom wall; and
(b) a locking member comprising a resiliently movable band disposed in the channel and extending along a side wall of the channel and away from a respective one of said apertures, said locking member being effective, when a bone fastener is driven through a said aperture into bone structure of a recipient user to, automatically and as a consequence of driving such bone fastener, activate a locking feature of said bone support assembly effective to prevent the bone fastener from withdrawing out of said bone support assembly and past said locking member.

* * * * *